(12) United States Patent
Zyzak et al.

(10) Patent No.: US 7,867,529 B2
(45) Date of Patent: *Jan. 11, 2011

(54) METHOD FOR REDUCING ACRYLAMIDE IN FOODS, FOODS HAVING REDUCED LEVELS OF ACRYLAMIDE AND ARTICLE OF COMMERCE

(75) Inventors: David Vincent Zyzak, Mason, OH (US); Robert Alan Sanders, Fairfield, OH (US); Marko Stojanovic, Cincinnati, OH (US); David Cammiade Gruber, Cincinnati, OH (US); Peter Yau Tak Lin, Liberty Township, OH (US); Maria Dolores Martinez-Serna Villagran, Mason, OH (US); John Keeney Howie, Oregonia, OH (US); Richard Gerard Schafermeyer, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 12/390,540

(22) Filed: Feb. 23, 2009

(65) Prior Publication Data

US 2009/0191310 A1  Jul. 30, 2009

Related U.S. Application Data

(63) Continuation of application No. 10/606,137, filed on Jun. 25, 2003, now Pat. No. 7,524,519.

(60) Provisional application No. 60/412,307, filed on Sep. 20, 2002, provisional application No. 60/421,432, filed on Oct. 25, 2002, provisional application No. 60/431,147, filed on Dec. 5, 2002.

(51) Int. Cl.
  *A23B 7/155* (2006.01)
  *A23J 3/34* (2006.01)
  *A23L 1/217* (2006.01)
  *A23L 3/3571* (2006.01)
  *A23L 1/212* (2006.01)
  *A23L 1/00* (2006.01)

(52) U.S. Cl. .............. 426/52; 426/549; 426/61; 426/438; 426/615; 426/618; 426/496

(58) Field of Classification Search ............ 426/20, 426/52, 56, 61, 106, 549, 618, 641, 656, 426/658, 808, 438

See application file for complete search history.

(56) References Cited

U.S. PATENT DOCUMENTS 2,490,431 A    12/1949  Greene et al.

(Continued)

FOREIGN PATENT DOCUMENTS

WO    WO 96/01572 A1    1/1996
WO    WO 01/91581 A3    12/2001
WO    WO 2004/004484 A3    1/2004

OTHER PUBLICATIONS

Fellows, P. "Food Processing Technology: Principles and Practice.", 2nd Edition, Woodhead Publishing, 2000, p. 350.*

(Continued)

*Primary Examiner*—Rena L Dye
*Assistant Examiner*—Viren Thakur
(74) *Attorney, Agent, or Firm*—Cynthia L. Clay; Adam W Borgman; Kim William Zerby

(57) ABSTRACT

A method for the reduction of acrylamide in food products, food products having reduced levels of acrylamide, and an article of commerce. In one aspect, the method comprises reducing the level of asparagine in a food material before final heating (e.g., cooking). In another aspect, the method comprises adding to a food material an enzyme capable of hydrolyzing the amide group of free asparagine. In yet another aspect, an article of commerce communicates to the consumer that a food product has reduced or low levels of acrylamide or asparagine.

20 Claims, 3 Drawing Sheets

U.S. PATENT DOCUMENTS

| | | | |
|---|---|---|---|
| 2,704,257 | A | 3/1955 | DeSollano et al. |
| 2,759,832 | A | 8/1956 | Cording et al. |
| 2,780,552 | A | 2/1957 | Willard et al. |
| 2,905,559 | A | 11/1958 | Andersen et al. |
| 3,085,020 | A | 4/1963 | Backinger et al. |
| 3,369,908 | A | 2/1968 | Gonzales et al. |
| 3,690,895 | A | 9/1972 | Amadon et al. |
| 3,917,866 | A | 11/1975 | Purves et al. |
| 3,987,210 | A | 10/1976 | Cremer |
| 3,998,975 | A | 12/1976 | Liepa |
| 4,210,594 | A | 7/1980 | Logan et al. |
| 4,272,554 | A | 6/1981 | Schroeder et al. |
| 4,985,269 | A | 1/1991 | Irvin et al. |
| 5,356,646 | A | 10/1994 | Simic-Glavaski et al. |
| 5,464,642 | A | 11/1995 | Villagran et al. |
| 5,464,643 | A | 11/1995 | Lodge |
| 5,558,886 | A | 9/1996 | Martinez-Bustos et al. |
| 6,066,353 | A | 5/2000 | Villagran et al. |
| 6,068,873 | A | 5/2000 | Deirue et al. |
| 6,287,622 | B1 | 9/2001 | Villagran et al. |
| 6,528,768 | B1 | 3/2003 | Simic-Glavaski et al. |
| 7,514,113 | B2 | 4/2009 | Zyzak et al. |
| 7,524,519 | B2 | 4/2009 | Zyzak et al. |
| 2004/0058046 | A1 | 3/2004 | Zyzak et al. |
| 2004/0058054 | A1 | 3/2004 | Elder et al. |

OTHER PUBLICATIONS

Lawrence, James E., "Acrylamide in Food Update", Health Canada, 1 pg. dated Sep. 11, 2002.

FAO/WHO Consultation on the Health Implications of Acrylamide in Food: Summary Report; Geneva Switzerland, Jun. 25-27, 2002.

Talburt & Smith; "Potato Processing"; 4$^{th}$ Edition, 1987.

Watson, S.A.; "Corn: Chemistry and Technology"; American Association of Cereal Chemists, 1987; pp. 410-420.

Zyzak, David A. et al.; "Acrylamide Formation Mechanism in Heated Foods"; 2003 Journal of Agricultural and Food Chemistry; vol. 51, No. 16, pp. 4782-4787.

Biederman, Maurus, et al.; "Methods for Determining the Potential of Acrylamide Formation and Its Elimination in Raw Materials for Food Preparation, such as Potatoes"; Official Food Control Authority of the Canton of Zurich, 2002.

Biederman, Maurus, et al.; "Experiments on Acrylamide Formation and Possibilities to Decrease the Potential of Acrylamide Formation in Potatoes"; Official Food Control Authority of the Canton of Zurich, 2002.

Nielsen, Monk; "Enzyme Technology for Production of Protein Based Flavours"; Novo Nordisk; 1995.

www.Foodstandards.gov.uk; "Food Standards Agency Study of Acrylamide in Food Background Information and Research Findings"; Press Briefing May 17, 2002.

European Commission; Health & Consumer Protection Directorate—General; "Opinion of the Scientific Committee on Food on New Findings Regarding the Presence of Acrylamide in Food"; Jul. 3, 2002.

Institute of Food Science & Technology (UK); "Additional Research on Acrylamide in Food Essential, Scientists Declare"; Joint Press Release FAO/WHO/51; Jun. 27, 2002.

www.cspinet.org; Center for Science in the Public Interest; "New Tests Confirm Acrylamide in American Foods"; Jun. 25, 2002.

Tareke, Eden, et al.; "Analysis of Acrylamide, a Carcinogen Formed in Heated Foodstuffs"; Journal of Agricultural and Food Chemistry, pp. A-1; 2002.

Sanders, R. A., et al.; "An LC/MS Acrylamide Method and It's Use in Investigating the Role of Asparagine", Presented Sep. 26, 2002.

* cited by examiner

Figure 2 Mode of action for asparaginase

METHOD FOR REDUCING ACRYLAMIDE IN FOODS, FOODS HAVING REDUCED LEVELS OF ACRYLAMIDE AND ARTICLE OF COMMERCE

CROSS REFERENCE TO RELATED APPLICATIONS

This application is a continuation application of U.S. application Ser. No. 10/606/137, filed Jun. 25, 2003, now U.S. Pat. No. 7,524,519 which claims the benefit of priority to: U.S. Provisional Application Ser. No. 60/412,307, filed Sep. 20, 2002; U.S. Provisional Application Ser. No. 60/421,432, filed Oct. 25, 2002; and U.S. Provisional Application Ser. No. 60/431,147, filed Dec. 5, 2002, all of which are herein incorporated by reference.

FIELD OF INVENTION

The present invention relates to the reduction of acrylamide in food products and to food products having reduced levels of acrylamide. The invention further relates to an article of commerce.

BACKGROUND OF THE INVENTION

Since the dawn of civilization, carbohydrate-containing foods have been a staple in man's diet. Today, carbohydrate-containing foods such as breads, breakfast cereals, biscuits, crackers, cookies, French fries, cooked starchy vegetables, taco shells, and snack foods are popularly consumed. Although such foods have been part of the human diet for countless years, researchers have only recently discovered that many of these foods contain acrylamide.

In April 2002, the Swedish National Food Administration and researchers from Stockholm University announced their findings that acrylamide, a potentially cancer-causing chemical, is formed in many types of cooked foods. Acrylamide has a carcinogenic potency in rats that is similar to that of other carcinogens in food, but for humans, the relative potency in food is not known. Only limited human population data are available for acrylamide and these provide no evidence of cancer risk from occupational exposure. (*FAO/WHO Consultation on the Health Implications of Acrylamide in Food: Summary Report*; Geneva, Switzerland, 25-27 Jun. 2002.)

Although further research is needed to assess what health effects, if any, may result from human consumption of acrylamide at the levels commonly found in such foods, many consumers have voiced concern. Accordingly, it is an object of the present invention to provide a method for reducing the level of acrylamide in foods. It is also an object of the present invention to provide food products having reduced levels of acrylamide. Further, it is an object of the present invention to provide an article of commerce that communicates to the consumer that a food product has reduced or low levels of acrylamide.

SUMMARY OF THE INVENTION

In one aspect, the present invention provides a method for reducing the level of acrylamide in a food product. In one embodiment, the method comprises adding an asparagine-reducing enzyme to the food material before heating.

In another aspect, the present invention provides a method for reducing the level of asparagine in a food material. In one embodiment, the method comprises adding an asparagine-reducing enzyme to the food material before heating.

In another aspect, the present invention provides food products having reduced levels of acrylamide.

In yet another aspect, the present invention provides an article of commerce that communicates to the consumer that a food product has reduced or low levels of acrylamide or of asparagine.

All documents cited herein are, in relevant part, incorporated herein by reference; the citation of any document is not to be construed as an admission that it is prior art with respect to the present invention.

DETAILED DESCRIPTION OF THE INVENTION

Applicants have discovered that asparagine, a naturally occurring amino acid found in virtually all living systems, can form acrylamide when heated. Thus, foods richer in asparagine, when heated, tend to contain higher levels of acrylamide; this is especially the case when asparagine-containing foods are heated in the presence of reducing sugars. Formation of acrylamide has also been found to be higher when foods are cooked to a lower final moisture content.

Figure 1:
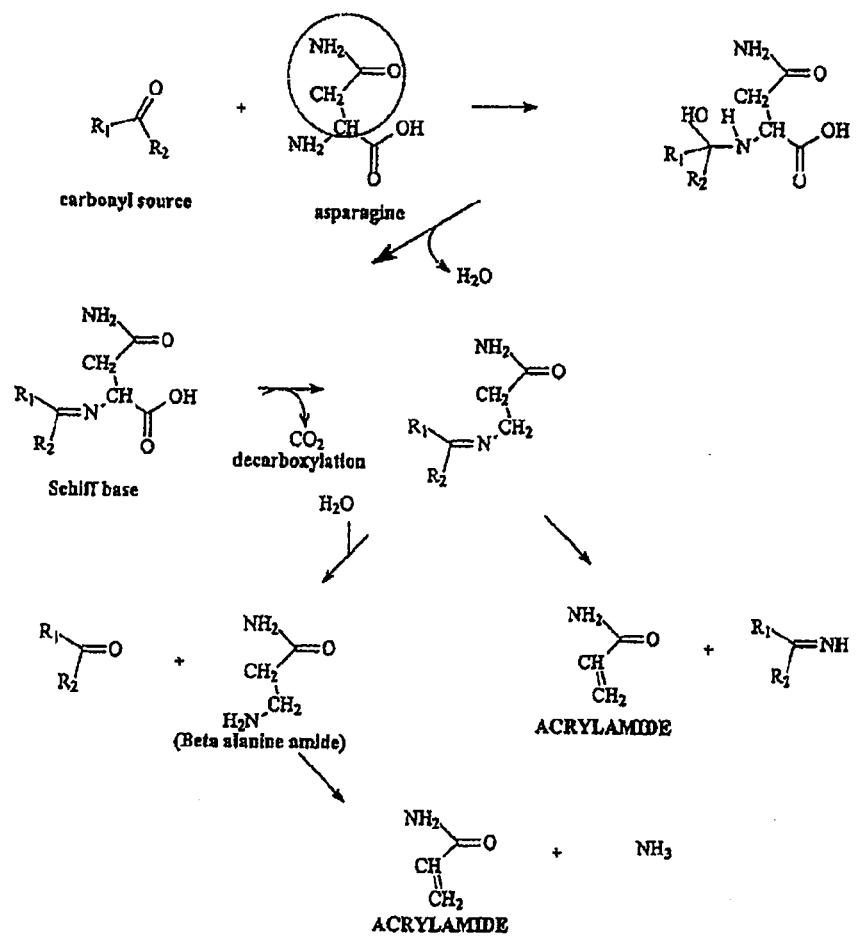
FIG. 1 sets forth the proposed reaction mechanism by which acrylamide forms from asparagine and a carbonyl source (such as glucose). $R_1$ and $R_2$ can=H, $CH_3$, $CH_2OH$, $CH_2(CH_2)_nCH_3$, or any other component making up a reducing sugar; n can be any integer less than 10.

While not being limited by theory, it is believed that acrylamide forms in food products via the reaction mechanism set forth in FIG. 1. It is believed that the alpha-amine group of free asparagine reacts with a carbonyl source, forming a Schiff base. Under heat, the Schiff base adduct decarboxylates, forming a product that can either: (1) hydrolyze to form beta-alanine amide (which can, under heat, further degrade to form acrylamide) or (2) decompose to form acrylamide and the corresponding imine. (Applicants have discovered that the circled precursor atoms comprise the carbons and nitrogens in acrylamide.)

Accordingly, Applicants have further discovered that acrylamide formation in heated foods can be reduced by removing the asparagine or converting the asparagine in the food to another substance before cooking. When such foods containing reduced levels of asparagine are heated, the amount of acrylamide formed is reduced.

Figure 2:
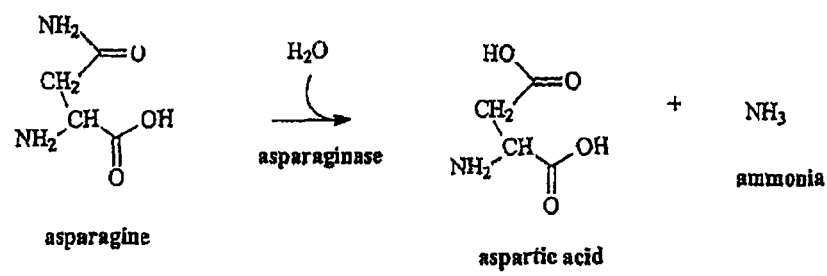
FIG. 2 sets forth the proposed reaction mechanism by which asparaginase reacts with asparagine to prevent the formation of acrylamide.

Applicants have found that adding an enzyme that hydrolyzes the amide group on the side chain of asparagine prior to heating (e.g., cooking) the food reduces the level of acrylamide present in the finished food product. While not being limited by theory, it is believed that the addition of such an enzyme degrades the side chain of asparagine, thus preventing the asparagine from forming acrylamide. In doing so, the amide bond is hydrolyzed and asparagine is converted to aspartic acid. This reaction mechanism is set forth in FIG. 2.

Preferred enzymes for use in the method herein include, but are not limited to, asparaginase. However, any enzyme capable of hydrolyzing the amide group of free asparagine to prevent the formation of acrylamide is within the scope of the present invention.

The advantages of using enzymes in food processing are numerous. These advantages include: (a) they are natural, nontoxic substances; (b) they generally catalyze a given reaction without causing unwanted side reactions; (c) they are active under very mild conditions of temperature and pH; (d) they are active at low concentrations; (e) the rate of reaction can be controlled by adjusting temperature, pH, and the amount of enzyme employed; and (f) they can be inactivated after the reaction has proceeded to the desired extent. (*Food Chemistry,* 4th Ed., Owen R. Fennema, Ed., Marcel Dekker, Inc., New York, 1985, pp. 427, 433.)

A. Method for Reduction of Acrylamide in Food Products

In one aspect, the present invention provides a method for the reduction of acrylamide in a food product. In one embodiment, the method comprises reducing the level of asparagine in a food material before final heating (e.g., cooking). In another aspect, the method comprises adding to a food material an enzyme capable of hydrolyzing the amide group of free asparagine. The preferred enzyme is asparaginase.

In another aspect, the present invention provides a method for the reduction of asparagine in a food product. In one embodiment, the method comprises adding to a food material an enzyme capable of hydrolyzing the amide group of free asparagine. The preferred enzyme is asparaginase.

In a preferred embodiment, the present invention provides a method for reducing the level of acrylamide in food, comprising:

(1) adding an asparagine-reducing enzyme to a food material, wherein said food material comprises asparagine;
(2) optionally mixing the enzyme with the food material;
(3) allowing a sufficient time for the enzyme to react with the asparagine;
(4) optionally deactivating or optionally removing the enzyme; and
(5) heating the food material to form the finished food product.

1. Adding an Asparagine-reducing Enzyme to a Food Material, wherein said Food Material Comprises Asparagine As used herein, "asparagine-reducing enzyme" includes any enzyme capable of reducing the level of asparagine in a food product. In one embodiment, the asparagine-reducing enzyme is an enzyme capable of hydrolyzing the amide group of free asparagine. A preferred enzyme for use herein is asparaginase. A preferred source of asparaginase is Sigma-Aldrich, catalog #A2925.

As used herein, the terms "asparagine-reducing enzyme" and "enzyme" include one or more enzymes; for example, a mixture of two or more enzymes is encompassed by the terms. For example, deamidases that have asparagine-reducing functionality are included in the terms.

As used herein, "food material" includes, but is not limited to, any edible material used in the preparation of food, including mixtures of two or more foods. "Food material" includes any type of asparagine-containing food, food product, food ingredient, or mixtures thereof. The food material can be in any suitable form, including raw or pre-treated. Suitable methods of pre-treating the food material include, but are not limited to, blanching, steaming, boiling, chopping, macerating, comminuting, reducing the particle size, drying with heat, and combinations thereof.

The enzyme may be added to the food material in any suitable form. For instance, the enzyme may be added as a powder or in the form of a solution. Furthermore, the enzyme may be added to the food material in any suitable manner, such as directly (for example, sprinkled, poured, or sprayed on the food material) or indirectly. In one embodiment, the enzyme is admixed with a food that does not contain asparagine, then the resulting mixture is added to the asparagine-containing food. In another embodiment, at least a portion of the asparagine is extracted from the food material, the resulting extract is treated with the enzyme, then at least a portion of the extract is added back into at least a portion of the food material; for example, the enzyme may be added to the stream, or the stream may be pumped through a bed or column of immobilized enzyme (enzyme either adsorbed or chemically bonded to a substrate, preferably an inert substrate, e.g., pieces of plastic or beads in a column). As used herein, "adding" the enzyme to the food material includes, but is not limited to, any means of bringing the asparagine and the enzyme together.

The enzyme may be added to the food material at any suitable stage of the method. For example, the enzyme may be added with the other ingredients during the mixing of a dough. In one embodiment, enzyme can be added to a food material before, during, or after maceration. In another embodiment, the food material is soaked in water before the enzyme is added.

Enzymes are marketed by units of activity, rather than by weight or volume. Thus, the effective amount of enzyme required to achieve the desired level of acrylamide reduction in the finished food product will depend upon the activity of the particular enzyme product used.

The amount of enzyme to add can depend upon the level of asparagine reduction, and accordingly the level of acrylamide reduction, that is desired. The amount of enzyme to add can also depend upon the amount of asparagine present in the food material; food materials higher in asparagine will generally require increased levels of enzyme or increased reaction time to achieve the same level of acrylamide reduction. The amount of enzyme to add can also depend upon the particular enzyme used (for example, the particular enzyme's ability to degrade asparagine) and the particular food material treated. One skilled in the art will be able to determine the effective amount of enzyme based upon the specific food material, the specific enzyme, the enzyme's specific activity, and the desired result.

2. Optionally Mixing the Enzyme with the Food Material

Optionally but preferably, the enzyme is thoroughly mixed with the food material. Any suitable method of mixing can be used. In one embodiment, mixing is carried out simultaneously with the maceration of the food material and the addition of the enzyme. In another embodiment, the enzyme is dissolved in water prior to addition to the food material.

3. Allowing a Sufficient Time for the Enzyme to React with the Asparagine

The amount of time needed for the enzyme to react with the asparagine will depend upon factors including, but not limited to, the desired level of acrylamide reduction, the characteristics of the particular food material (e.g., chemical composition, amount of asparagine present, particle size), and the particular enzyme added. Preferably, the enzyme is allowed to react for a sufficient amount of time to result in a food material wherein the level of asparagine has been reduced by at least about 10%, preferably at least about 30%, more preferably at least about 50%, still more preferably at least about 70%, and even more preferably at least about 90%. In general, the longer the enzyme is allowed to react, the greater the level of asparagine reduction and thus the greater the level of acrylamide reduction. The step of allowing a sufficient time for the enzyme to react can be carried out in any suitable manner; for example, it can be carried out simultaneously with adding the enzyme to the food material, mixing the enzyme with the food material, or combinations thereof.

As known in the art, pH and temperature are factors that affect enzymatic activity. One skilled in the art should readily be able to determine optimal conditions of these and other parameters (e.g., water content). In addition, optimal pH and temperature conditions for specific enzymes are typically available in the literature and/or from enzyme suppliers.

4. Optionally Deactivating or Optionally Removing the Enzyme

After the enzyme has reacted to the desired extent, it can optionally be inactivated or removed from the food material. When an enzyme that is safe for consumption (e.g., naturally occurring and found in common foods) is used, one may choose not to deactivate or remove the enzyme. Alternatively, the enzyme can be deactivated by any suitable means that inactivates the enzyme. For example, the enzyme can be deactivated through the use of heat, pH adjustment, treatment with a protease, or combinations thereof. Furthermore, the enzyme can be removed from the food material by any suitable means including, but not limited to, extraction. The enzyme can be deactivated, removed, or subjected to a combination of deactivation and removal.

5. Heating the Food Material to Form the Finished Food Product

The food material can then be heated in the usual manner, such as by baking, frying, extruding, drying (e.g., via vacuum oven or drum dryer), puffing, or microwaving. At least a portion of the enzyme may be added to the food material during the heating step. Deactivating the enzyme may occur through heating, thus the optional deactivation step and the cooking step may be carried out simultaneously. Heat processing via cooking can denature and inactivate the enzyme such that the food material is not subjected to continuing enzymatic activity. Furthermore, at least a portion of the time allowed for enzymatic reaction may be carried out during the heating step.

As used herein the term "finished food product" or "food product" includes, but is not limited to, foods ready for consumption and foods to be used as ingredients to prepare other foods.

Preferably, the level of acrylamide in the finished food product is reduced by at least about 10%, preferably at least about 30%, more preferably at least about 50%, still more preferably at least about 70%, and even more preferably at least about 90%.

B. Means of Practicing the Method

The present invention can be practiced by any suitable means. For example, the method herein can be practiced in batch, semi-batch, or continuous mode.

C. Food Products Having Reduced Levels of Acrylamide

Food products prepared according to the method herein can have a reduction in the acrylamide level of at least about 10%, preferably at least about 30%, more preferably at least about 50%, still more preferably at least about 70%, and even more preferably at least about 90%.

The method herein can be applied to the production of any suitable food product, including but not limited to carbohydrate-containing foods, especially low-moisture foods (e.g., less than about 10%), that are heated during preparation. For instance, the method can be used to reduce the level of acrylamide found in mashed potatoes, potato chips, fabricated snack foods, French fries, breakfast cereals, breads, cookies, crackers, toaster pastries, pizza crust, pretzels, hash browns, tater tots, corn tortillas, and taco shells.

In one embodiment, fried fabricated potato crisps have less than about 400 ppb acrylamide, preferably less than about 300 ppb, more preferably less than about 200 ppb, still more preferably less than about 50 ppb, and most preferably less than about 10 ppb.

In yet another embodiment, French fries made from cut potatoes have less than about 40 ppb acrylamide, preferably less than about 30 ppb, more preferably less than about 20 ppb, and most preferably less than about 10 ppb.

In still another embodiment, tortilla chips and corn chips have less than about 75 ppb acrylamide, preferably less than about 50 ppb, and more preferably less than about 10 ppb.

Although the method herein will generally be described in terms of preferred potato food products and tortilla chips, it should be understood by one skilled in the art that the method herein can be applied to any suitable food product. Non-limiting examples include crackers, breads (e.g., rye, wheat, oat, potato, white, whole grain products, mixed flours, loaves, twists, buns, rolls, pitas, matzos, focaccia, melba toast, zwieback, croutons, soft pretzels, soft and hard bread sticks, heat and serves), toaster pastries, cookies, danish, croissant, tarts, pie crusts, pastries, muffins, brownies, sheet cakes, donuts, snack foods (e.g., pretzels, tortilla chips, corn chips, potato chips, fabricated snacks, fabricated potato crisps, extruded snacks, extruded filled snacks, trail mix, granola, snack mixes, shoe-string potatoes), flours, corn meal, polenta, mixes (e.g., cake mixes, biscuit mixes, brownie mixes, bread mixes, pancake mixes, crepe mixes, batter mixes, pizza dough), refrigerated doughs (e.g., biscuits, breads, bread sticks, croissants, dinner rolls, pizza dough, cookies, danish, brownies, pie crust), frozen foods (e.g., pie crusts, pies, tarts, turnovers, pizzas, food pockets, cakes, French fries, hash browns, breaded products such as chicken and fish, breaded vegetables), bagels, breakfast cereals, biscuits, French fries, vegetables (e.g., dried, grilled, roasted, broiled, fried, vacuum dried), taco shells, hash browns, mashed potatoes, toast, grilled sandwiches, flour and corn tortillas, crepes, pancakes, waffles, batters, pizza crust, rice, herbs, spices, nuts, nut-based foods (e.g, peanut butter, foods containing chopped nuts), fruit (e.g., dried, grilled, roasted, broiled, fried, vacuum dried, baked, jellies, pie fillings, flambés, raisins), hush puppies, alcoholic beverages (e.g., beers and ales), products comprising roasted cocoa beans (e.g., cocoa, chocolates, confectionary coatings, hot chocolate, hot chocolate mixes, candy bars), and animal foods (e.g., dog food, cat food, ferret food, guinea pig food, gerbil food, hamster food, bird food, llama food, ostrich food, emu food, cattle food, deer food, elk food, buffalo food, rabbit food, rat food, mouse food, chicken food, turkey food, pig food, horse food, goat food, sheep food, monkey food, fish food).

1. Dehydrated Potato Products

The present invention can be used to make dehydrated potato products having reduced levels of acrylamide. The following sets forth a preferred method of making such dehydrated potato products, but the present invention is not limited to this particular embodiment. Although the embodiment set forth in detail below describes addition of enzyme before the cooked potatoes are comminuted, it should be understood that enzyme may be added at any suitable stage of any suitable process for making dehydrated potato products. For instance, enzyme may be added to the potatoes before cooking, after cooking, before comminution, after comminution, or during any other suitable processing step before the final dehydrated potato product is formed. Furthermore, non-limiting examples of other embodiments may comprise: (a) adding enzyme to raw potato followed by conventional dehydrated potato processing, (b) adding enzyme to raw potato followed by shredding or thinly slicing and conventional processing, (c) adding enzyme to raw potato followed by shredding or thinly slicing, then blanching, then followed by conventional processing, (d) adding enzyme to blanched, shredded, or thinly sliced potato followed by conventional processing, or (e) any other suitable means of adding enzyme. The method herein may also be practiced with any suitable method for making dehydrated potato products known in the art, such as those set forth in *Potato Processing*, 4th Ed., Talburt and Smith, Eds., AVI Books, Van Nostrand Reinhold Co., New York, 1987, [hereinafter "*Potato Processing*"], at pp. 535-646.

In a preferred embodiment, dehydrated potato products, such as potato flakes, flanules, or granules, can be made in accordance with the following method. In general, the method comprises: (1) cooking potatoes; (2) adding an asparagine-reducing enzyme to the cooked potatoes; (3) forming a wet mash; and (4) drying the mash to form dehydrated potato products.

Any suitable potatoes, such as those used to prepare conventional potato flakes, flanules, or granules, can be used to prepare the dehydrated potato products herein. Preferably, the dehydrated potato products are prepared from potatoes such as, but not limited, to Norchip, Norgold, Russet Burbank, Lady Rosetta, Norkotah, Sebago, Bintje, Aurora, Saturna, Kinnebec, Idaho Russet, Altura, Russet Norkotah, Atlantic, Shepody, Asterix, and Mentor.

Potatoes having less than about 5% reducing sugars (calculated on a dehydrated potato basis), preferably less than about 3%, and more preferably less than about 2%, are preferred. For example, potatoes having low levels of reducing sugars (i.e. <1.5%) are especially preferred for fried potato snacks.

The potatoes are subjected to cooking to soften them for mashing. The potatoes may be peeled, partially peeled, or unpeeled. The potatoes may be whole or may be sliced into pieces of any size before cooking. The cooking procedure can be any thermal or other type of cooking process that softens the potatoes for mashing. For instance, the potatoes may be cooked by submersion in water or steam.

For example, potato slices having an average thickness of about ⅜ inch to about ½ inch are typically cooked with steam having a temperature of from about 200° F. (93° C.) to about 250° F. (121° C.) from about 12 to about 45 minutes, more particularly from about 14 to about 18 minutes. Shoestring cut potatoes pieces are typically cooked with steam having a temperature of from about 200° F. (93° C.) to about 250° F. (121° C.) for about 7 to about 18 minutes, more particularly from about 9 to about 12 minutes, to achieve the desired hardness.

Next, an effective amount of enzyme, preferably asparaginase, is added to the cooked potatoes. Depending upon the functional temperature range of the asparagine-reducing enzyme to be used, the cooked potatoes may first require temperature adjustment before addition of the enzyme. The cooked potatoes are then comminuted to produce a wet mash. Comminution of the cooked potatoes may be accomplished by any suitable means, such as but not limited to ricing, mashing, shredding, or a combination thereof.

Optional ingredients can be added and mixed into the wet mash. Such optional ingredients can include starch. Starch can include, but is not limited to, any suitable native or modified starch, including any dried potato products that are added into or back into the mash. Emulsifier can also optionally be added to the wet mash as a processing aid.

After the mash is formed, it can be further dried and processed as described below to form dehydrated potato products. Alternatively, the wet mash can be used to produce products such as, but not limited to, mashed potatoes, potato patties, potato pancakes, and potato snacks such as extruded French fries, potato sticks, and snack chips.

For example, the wet potato mash can be used to produce extruded French fried potato products such as those described in U.S. Pat. No. 3,085,020, issued Apr. 9, 1963 to Backinger et al.

After forming the mash, the mash is dried to form dehydrated potato products. These dehydrated potato products can be in any form, such as but not limited to flakes, flanules, granules, agglomerates, sheets, pieces, bits, flour, or particulates.

Any suitable procedure, such as those known in the art, for producing such dehydrated potato products from a mash may be employed, and any suitable equipment may be used. For example, the mash can be dried to produce flakes according to known processes such as those described in U.S. Pat. No. 6,066,353, issued May 23, 2000 to Villagran, et al., as well as those processes described in U.S. Pat. Nos. 2,759,832 issued Aug. 19, 1956 to Cording et al., and 2,780,552 issued Feb. 5, 1957 to Willard et al. The mash can be dried to make flanules according to the process set forth in U.S. Pat. No. 6,287,622, issued Sep. 11, 2001 to Villagran et al. Granules can be produced by processing the mash according to the process described in U.S. Pat. No. 3,917,866, issued Nov. 4, 1975 to Purves et al., or by other known processes such as that described in U.S. Pat. No. 2,490,431 issued Dec. 6, 1949 to Greene et al. Suitable dryers can be selected from those well known drying devices including but not limited to fluidized bed dryers, scraped wall heat exchangers, drum dryers, freeze-dryers, air lift dryers, and the like.

Preferred drying methods include those that reduce the amount of total thermal input. For example, freeze drying, drum drying, resonant or pulse flow drying, infrared drying, or a combination thereof is preferred when producing flakes; and air lift drying, fluidized bed drying, or a combination thereof is preferred when producing granules.

Although the dehydrated potato products herein will be primarily described in terms of flakes, it should be readily apparent to one skilled in the art that the potato mash of the present invention can be dehydrated to produce any desired dehydrated potato product that can be derived from a mash.

Drum drying, such as with drum dryers commonly used in the potato product industry, is the preferred method for drying the potato mash to form flakes. The preferred process utilizes a single drum drier wherein the wet potato mash is spread onto the drum in a thin sheet having a thickness of from about 0.005" to about 0.1", preferably from about 0.005" to about 0.05", more preferably about 0.01". Typically, when a drum dryer is used, the mash is fed to the top surface of the drum by a conveying means. Small diameter unheated rolls progressively apply fresh potato mash to portions already on the drum, thus building up a sheet, or layer, having a predetermined thickness. The peripheral speed of the small rolls is the same as that of the drum. After the layer of mash travels around a portion of the circumference of the drum, a doctor knife removes the dried sheet by peeling the dried sheet away from the drum. Typically, the drum dryer itself is heated to temperatures in a range of from about 250° F. (121° C.) to about 375° F. (191° C.), preferably from about 310° F. (154° C.) to about 350° F. (177° C.), and more preferably from about 320° F. (160° C.) to about 333° F. (167° C.) by pressurized steam contained within the drum at pressures of from about 70 psig to about 140 psig. For best results, the rotational speed of the dryer drum and the internal temperature thereof are suitably controlled so as to give a final product having a moisture content of from about 5% to about 14%, preferably from about 5% to about 12%. Typically, a rotational speed of from about 9 sec/rev to about 25 sec/rev., preferably about 11 sec/rev to about 20 sec/rev, is sufficient.

Once the wet mash is sheeted and dried, the resulting dried sheet of flakes can then be broken into smaller sections if desired. These smaller sections can be of any desired size. Any method of breaking the sheet that minimizes starch and potato cell damage, such as fracturing, grinding, breaking, cutting, or pulverizing, can be used. For example, the sheet can be comminuted with an Urschel Comitrol™, manufactured by Urschel Laboratories, Inc. of Valparaiso, Ind., to break up the sheet. Alternatively, the sheet of flakes can be left intact. As used herein, both the intact sheet of flakes and smaller sheet sections are included in the term "potato flakes."

2. Foods Made from Dehydrated Potato Products

The asparagine-reduced dehydrated potato products can be used to make any suitable food product. An especially preferred use of the dehydrated potato products is in the production of fabricated snacks made from a dough, preferably fabricated chips. Examples of such fabricated chips include those described in U.S. Pat. No. 3,998,975 issued Dec. 21, 1976 to Liepa, U.S. Pat. No. 5,464,642 issued Nov. 7, 1995 to Villagran et al., U.S. Pat. No. 5,464,643 issued Nov. 7, 1995 to Lodge, and WO 96/01572 published Jan. 25, 1996 by Dawes et al.

Additional enzyme can also be added to the dough ingredients. In one embodiment, the fabricated snack is made by the method comprising:

(1) adding an asparagine-reducing enzyme to a dough;
(2) forming a snack piece from the dough; and
(3) cooking the snack piece to form a fabricated snack.

Cooking can be performed by any suitable method, for instance by frying, baking, or a combination of frying or baking. Furthermore, the forming and cooking steps can be carried out simultaneously, such as with extruded snack products.

In another embodiment, the fabricated snack is made by the method comprising:

(1) blending dry ingredients;
(2) optionally adding emulsifier to dry ingredients;
(3) adding water;
(4) mixing to form a dough;
(5) forming a dough sheet;
(6) forming a snack piece from the dough sheet; and
(7) cooking the snack piece to form a fabricated snack.

Enzyme can be added at any suitable stage of the process, for instance enzyme may be added during the blending, optionally adding emulsifier, adding water, mixing, and/or forming steps. Alternatively, the enzyme can be applied, preferably as a solution, to the dough surface; this can occur either before or after the snack pieces are formed from the dough sheet. In one embodiment, the enzyme solution is added to the surface of the dough sheet.

The dehydrated potato products can also be rehydrated and used to produce food products such as mashed potatoes, potato patties, potato pancakes, and other potato snacks such as extruded French fries and potato sticks. For example, dehydrated potato products can be used to produce extruded French fried potato products such as those described in U.S. Pat. No. 3,085,020, issued Apr. 9, 1963 to Backinger et al., and U.S. Pat. No. 3,987,210, issued Oct. 18, 1976 to Cremer. The dehydrated potato products can also be used in breads, gravies, sauces, baby food, or any other suitable food product.

In another embodiment, conventional dehydrated potato products are used to make fabricated snacks from a dough, preferably fabricated chips. In this embodiment, an asparagine-reducing enzyme is added to the dough ingredients, then the dough is processed by any suitable means to make the fabricated snack.

3. Potato Chips

The present invention can be used to make potato chips having reduced levels of acrylamide. The following sets forth a preferred method of making such potato chip products, but the present invention is not limited to this particular embodiment. For example, enzyme may be added at any suitable processing stage of art-recognized potato-chipping methods, such as those set forth in *Potato Processing*, at pp. 371-489.

In a preferred embodiment, the present invention provides a method for reducing the level of acrylamide in potato chips, comprising:

(1) optionally peeling potatoes;
(2) optionally washing potatoes;
(3) slicing potatoes to form potato slices;
(4) optionally rinsing the potato slices;
(5) optionally blanching the potato slices;
(6) optionally cooling the potato slices;
(7) adding an acrylamide-reducing enzyme to the potato slices;
(8) optionally drying the potato slices;
(9) frying the potato slices to form potato chips.

Most preferably, the potato slices are blanched before the enzyme is added. Although the foregoing describes addition of enzyme at step (7) above, it should be understood that enzyme may be added at any suitable stage of the process. For instance, enzyme may be added to the potatoes before slicing, after slicing, after rinsing, during blanching, during cooling, or at any other suitable stage before drying, if the optional drying step is performed, or at any other suitable stage before frying if the potato slices are not optionally dried.

In another embodiment, potato slice blanching and soaking solutions containing asparagine are pumped through a column comprising immobilized asparagine-reducing enzyme. The effluent from the column is returned to the potato slices. The potato slices are then processed according to typical processing procedures. Practicing the method in this manner can return at least part of the native potato flavors back to the chip that may be lost during the blanching and enzyme treatment steps.

Potato chips made according to the method herein can have less than about 150 ppb acrylamide, preferably less than about 100 ppb, more preferably less than about 50 ppb, even more preferably less than about 10 ppb, and most preferably less than about 5 ppb.

4. French Fries

The present invention can be used to make French fries having reduced levels of acrylamide. The following sets forth a preferred method of making such French fries, but the present invention is not limited to this particular embodiment. For example, enzyme may be added at any suitable processing stage of art-recognized methods for making French fries, such as those set forth in *Potato Processing*, at pp. 491-534, or those methods described in U.S. Pat. Nos. 6,001,411 and 6,013,296.

In a preferred embodiment, the present invention provides a method for reducing the level of acrylamide in French fries, comprising:

(1) optionally peeling potatoes;
(2) optionally washing potatoes;
(3) cutting potatoes to form potato strips;
(4) optionally rinsing the potato strips;
(5) optionally blanching the potato strips;
(6) optionally cooling the potato strips;

(7) adding an acrylamide-reducing enzyme to the potato strips;

(8) optionally drying the potato strips;

(9) optionally coating the potato strips; and

(10) par-frying the potato strips to form par-fries.

The par-fries can then be frozen, packaged, and stored for later frying to form the final French fries.

Most preferably, the potato strips are blanched before the enzyme is added. If coated French fries are desired, a suitable coating material, such as starch or a blend of materials comprising one or more starches, can be used to coat the potato strips before par-frying. Although the foregoing describes addition of enzyme at step (7) above, it should be understood that enzyme may be added at any suitable stage of the process. For instance, enzyme may be added to the potatoes before cutting, after cutting, after rinsing, during blanching, during cooling, or at any other suitable stage before drying, if the optional drying step is performed, or at any other suitable stage before par-frying if the potato strips are not optionally dried. Although less preferred, enzyme may be added between the steps of par-frying and final frying to form the final French fries.

Finished French fries made from the par-fries of the present invention can have less than about 40 ppb acrylamide, preferably less than about 30 ppb, more preferably less than about 20 ppb, and most preferably less than about 10 ppb.

5. Tortilla Chips

Tortilla chips are particularly popular consumer snack products. Tortilla chips are traditionally made from whole kernel corn that has been cooked in a hot lime solution for about 5 to about 50 minutes, then steeped overnight. The cooking-steeping process softens the outer hull and partially gelatinizes the starch in the endosperm of the corn. This cooked-steeped corn, called "nixtamal," is then washed to remove the outer hull and ground to form a plastic dough, known as "masa," that contains about 50% moisture. The freshly-ground masa is sheeted, cut into snack pieces, and baked for about 15 to about 30 seconds at a temperature of from about 575° F. to about 600° F. (302° C. to 316° C.) to reduce the moisture content to from about 20% to about 35%. The baked snack pieces are then fried in hot oil to form tortilla chips having a moisture content of less than about 3%. See, e.g., U.S. Pat. No. 2,905,559, issued Nov. 1, 1958 to Anderson et al., U.S. Pat. No. 3,690,895, issued Sep. 12, 1972 to Amadon et al., and *Corn: Chemistry and Technology*, American Association of Cereal Chemists, Stanley A. Watson, et. al., Ed., pp. 410-420 (1987).

Tortilla chips can also be made from dried masa flour. In typical processes for making such dried masa flour, such as those described in U.S. Pat. No. 2,704,257 issued Mar. 1, 1955, to de Sollano et al., and U.S. Pat. No. 3,369,908, issued Feb. 20, 1968 to Gonzales et al., the lime-treated corn is ground and dehydrated to a stable form. The dried masa flour can be later rehydrated with water to form a masa dough that is then used to produce tortilla chips, such as those described in WO 01/91581, published Dec. 6, 2001, by Zimmerman et al.

In one embodiment, a tortilla chip made from masa is made by the method comprising:

(1) adding an asparagine-reducing enzyme to a dough comprising masa;

(2) forming a snack piece from the dough; and (3) cooking the snack piece to form a tortilla chip.

In another embodiment, a tortilla chip made from nixtamal is made by the method comprising:

(1) adding an asparagine-reducing enzyme to nixtamal;

(2) forming a snack piece from the nixtamal; and (3) cooking the snack piece to form a tortilla chip.

Enzyme can be added at any suitable stage of the process. In one embodiment, the enzyme solution is added to the surface of the dough sheet.

Cooking can be performed by any suitable method, for instance by frying, baking, or a combination of frying or baking. Furthermore, the forming and cooking steps can be carried out simultaneously, such as by extrusion.

In one embodiment, the tortilla chips have less than about 75 ppb acrylamide, preferably less than about 50 ppb, and more preferably less than about 10 ppb.

D. Article of Commerce

Another embodiment of the invention is an article of commerce comprising:

(a) a food product, wherein said food product has a reduced level of acrylamide;

(b) a container for containing the food product; and (c) a message associated with the container.

The message informs the consumer that the food product contains a reduced level of acrylamide. Suitable messages include, but are not limited to, messages that communicate "reduced" or "low" levels of acrylamide, messages that communicate that less than a specified amount of acrylamide is present (e.g., less than 5 ppb), and messages that communicate that the food product meets or exceeds a suggested or mandatory level (e.g., regulatory threshold or signal level). In one embodiment, the message informs the consumer that the food product is made with an ingredient or ingredients having reduced or low levels of asparagine, thus implying that the food product therefore has reduced or low levels of acrylamide.

In another embodiment, the article of commerce comprises:

(a) a food product, wherein said food product has a reduced level of asparagine;

(b) a container for containing the food product; and (c) a message associated with the container.

The message informs the consumer that the food product contains a reduced or low level of asparagine.

The message can be printed material attached directly or indirectly to the container, attached directly or indirectly near the container, or alternatively can be a printed, electronic, or broadcast message associated with the container.

Any container from which the food product can be dispensed, presented, displayed, or stored is suitable. Suitable containers include, but are not limited to, bags, canisters, boxes, bowls, plates, tubs, and cans.

Analytical Methods

Parameters used to characterize elements of the present invention are quantified by particular analytical methods. These methods are described in detail as follows.

1. Acrylamide

Method for Measuring Acrylamide (AA) in Food Products

Summary

Food products are spiked with 1-$^{13}$C-acrylamide ($^{13}$C-AA) and extracted with hot water. The aqueous supernatant is extracted three times with ethyl acetate, and the ethyl acetate extracts are combined and concentrated and analyzed by LC/MS with selected ion monitoring for specific detection of AA and $^{13}$C-AA.

Extraction of Sample

1. Weigh 6.00±0.01 g of sample into a 125-mL Erlenmeyer flask. Note: Place the sample into a food processor and pulse for 30 seconds so that the particle size is about ⅛ inch or less. If the sample is too small to be effectively ground in a food processor, place the sample in a new plastic bag (e.g., Whirl-Pak™ or equivalent) and pulverize with a rubber mallet until the particle size is ⅛ inch or less.
2. Add 120 µL of 100 ng/µL $^{13}$C-AA in de-ionized distilled water (ISTD 2), with an adjustable 1000-µL pipette (calibrated), directly onto the sample.
3. Using a dispenser, add 40 mL of de-ionized distilled water to the flask and cover with foil.
4. Place into a 65° C. water bath for 30 min.
5. With a dispenser, add 10 mL of ethylene dichloride to the flask, and homogenize with a Tekmar Tissumizer™ (SDT-1810) or Ultra-Turrax® (T18 Basic) for 30 seconds, or until uniform. Rinse the probe into the flask with deionized distilled water.
6. Place 25 g of the homogenate into an 8-dram vial
7. Tightly cap the tube and centrifuge for 30 minutes at 2500-5200 RPM.
8. Transfer 8 g of supernatant to another 8-dram vial being careful to avoid solid particles.
9. Add 10 mL of ethyl acetate with a dispenser, cap, and vortex for 10 seconds.
10. Allow any emulsion to break up; help by swirling or shaking once or twice and then allowing layers to split.
11. Transfer as much of the top layer (ethyl acetate) as possible to a scintillation vial, without transferring any liquid (water) from the interface. Extract twice more with 5-mL portions of ethyl acetate and add to the same scintillation vial. Then, add approximately 2 g of anhydrous sodium sulfate.
12. Concentrate the extract with a gentle stream of nitrogen in a 60-65° C. water bath to about 1 mL. Transfer the extract to a Pierce REACTI-VIAL™ or equivalent conical-shaped glass vial and further concentrate the extract to a final volume of approximately 100-200 µL. Place this extract into an autosampler vial with a conical sleeve.

Preparation of Standards

Stock Solutions and Internal Standards

| Solution | Weight | Volumetric Flask | Solvent | Concentration (ppm) |
|---|---|---|---|---|
| Stock 1 | 0.1000 g Acrylamide (AA) | 100-mL | Ethyl Acetate | 1000 |
| ISTD 1 | 0.0100 g $^{13}$C-Acrylamide | 100-mL | Ethyl Acetate | 100 |
| Stock 2 | 0.1000 g Acrylamide (AA) | 100-mL | Deionized Distilled Water | 000 |
| ISTD 2 | 0.0100 g $^{13}$C-Acrylamide | 100-mL | Deionized Distilled Water | 100 |

Intermediate Standards

| Solution | Volume Stock 1 AA (µL) | Volumetric Flask (mL) | Solvent | Concentration (ppm) |
|---|---|---|---|---|
| INT 1 | 100 | 10 | Ethyl Acetate | 10 |
| INT 2 | 1000 | 10 | Ethyl Acetate | 100 |

Calibration Standards

| Standard | Volume INT 1 (µL) | Volume INT 2 (µL) | Volume ISTD 1 (µL) | Volumetric Flask (mL) | Solvent | Conc. AA (ppm) | Conc. ISTD 1 (ppm) |
|---|---|---|---|---|---|---|---|
| 0 | 0 | 0 | 450 | 10 | Ethyl Acetate | 0 | 4.50 |
| 0.25 | 250 | 0 | 450 | 10 | Ethyl Acetate | 0.250 | 4.50 |
| 0.75 | 750 | 0 | 450 | 10 | Ethyl Acetate | 0.750 | 4.50 |
| 1.5 | 0 | 150 | 450 | 10 | Ethyl Acetate | 1.50 | 4.50 |
| 3.0 | 0 | 300 | 450 | 10 | Ethyl Acetate | 3.00 | 4.50 |
| 5.0 | 0 | 500 | 450 | 10 | Ethyl Acetate | 5.00 | 4.50 |

Homogenizer Cleaning Procedure

Use this cleaning procedure between every sample.
1. Fill a 1-L Erlenmeyer flask with hot tap water (≈80% full) and add a drop of Dawn™ dishwashing liquid (available from the Procter & Gamble Co.) or equivalent.
2. Insert the dispersing element probe into the water as far as possible.
3. Homogenize the solution for about 10-15 seconds.
4. Empty the cleaning solution from the Erlenmeyer; rinse and refill the flask with hot tap water.
5. Homogenize again for about 10-15 seconds.
6. Empty the flask and refill with hot tap water; homogenize again for about 10-15 seconds.
7. If the water is not clear and free of particulates, continue homogenizing clean hot tap water as many times as necessary to achieve this condition.
8. When the hot tap water is clear and free of particulates, rinse the probe with deionized distilled water.

Analysis by LC/MS

Samples are analyzed using a Waters 2690 LC interfaced to a Micromass LCZ mass spectrometer.

| | |
|---|---|
| Mobile Phase | 100% $H_2O$, 10 mM $NH_4Ac$, adjusted to pH 4.6 w/formic acid |
| Column | 2.0 mm × 150 mm, YMC C18 AQ (available from Waters Corp.) |
| Flow rate | 0.2 mL/min |
| Interface | Direct (no split) |
| Injection volume | 5 µL |
| MS ionization mode | Electrospray, positive ion mode |
| MS detection mode | Selected ion monitoring: m/z 72 (AA), m/z 73 ($^{13}$C-AA); dwell times: 0.5 s |

Data Analysis

Response ratios (area of AA peak/area of $^{13}$C-AA peak) are plotted against the corresponding concentration ratios for a series of five standards in ethyl acetate. All standards contain 4.5 μg/mL $^{13}$C-AA, and AA concentrations ranging from 0 to 5 μg/mL. Linear regression results in a calibration curve from which concentration ratios in extracts are determined from measured response ratios. When this concentration ratio is multiplied by the accurately known $^{13}$C-AA level (nominally 2 ppm) added to sample in step two of the extraction procedure, the level of AA in ppm results.

Sample Calculation for LC/MS:

The calibration curve is generated by plotting the response ratio (area m/z 72/area m/z 73) on the y axis vs. the concentration ratio ([AA]/[13C-AA]) on the x-axis. For this example, the equation of that line is y=0.899x+0.0123.

Measured area of AA peak (m/z 72) at 4.0 min: 100,000

Measured area of 13C-AA peak (m/z 73) at 4.0 min: 500,000

Response ratio $R_r$=0.200. From the slope and intercept of the calibration curve, the concentration ratio $R_c$ is calculated: $R_c$=(0.200−0.0123)/0.899=0.209

Given the spike level of 13C-AA in the sample (2 ppm), the measured level of AA is 0.209×2 ppm=0.418 ppm Quality Assurance/Quality Control (QA/QC)

1. All balances used in the preparation of standards and/or samples, must have their calibrations checked weekly with a set of qualified weights. The balances should be checked with at least three weights covering the range of sample/standard weights to be measured.
2. A six-point calibration curve should be performed daily.
3. A working reference material (WRM) should be analyzed with each set of samples. The concentration of this material should be within 2σ of the running mean. If it is not, the instrument should be recalibrated and the WRM recalculated.

2. Asparagine

Determination of Asparagine and Aspartic Acid in Food and Beverage Products

Principle

A weighed amount of sample is mixed with 5% HCl and heated for 30 minutes, then homogenized. A portion of the homogenate is centrifuged and then a portion of the supernatant is diluted and treated with FMOC reagent (9-fluorenylmethyl chloroformate), which reacts with asparagine and aspartic acid to form a highly fluorescent derivative. Reverse-phase HPLC is then used to resolve FMOC-asparagine from other sample matrix components. Detection is by fluorescence emission at 313 nanometers (nm) upon excitation at 260 nm. Analysis of standards of known concentration permits quantification.

Linearity

Working calibration curve of four standards (50-600ppm) give a correlation of 0.998 or better. A curve taken out to 2000 ppm also gives a correlation of 0.998.

Accuracy

Potato Products:

Potato starch is spiked with four levels of both asparagine and aspartic acid (40, 200, 400, and 600 ppm). Recovery of asparagine is 100% (Relative standard deviation of less than 4%) and recovery of aspartic acid is 110% (Relative standard deviation of less than 4%).

REFERENCES

1. Herbert, P.; Santos, L; Alves, A. Journal of Food Science (2001), 66(9), 1319-1325.
2. Heems, Dany; Luck, Geneviewe; Fraudeau, Chrisophe; Verette, Eric. Journal of Chromatography, A (1998), 798 (1+2), 9-17.

System Repeatability

A working reference material of potato chip is run in duplicate over five days. Results are as follows:

|  | ug/g asparagine | ug/g aspartic acid |
| --- | --- | --- |
| ave | 7832.07 | 1440.98 |
| STD | 625.59 | 195.80 |
| % RSTD | 7.99 | 13.59 |

Below are Suggested Chemicals and Equipment; However, Substitutions of Equivalent Materials are Acceptable.

| CHEMICALS | |
| --- | --- |
| Water, HPLC or Milli-Q ™ Grade (Millipore) | |
| Acetonitrile, HPLC Grade | Burdick & Jackson #AH015-4 |
| Methanol, HPLC Grade | Fisher #A452-4 |
| Ethyl Acetate | Baker #9280-3 |
| Pentane | Burdick & Jackson #GC312-4 |
| Asparagine monohydrate | EM Science |
| Aspartic acid | Sigma #A-8949 |
| aminoisobutyric acid | Sigma #A-8379 |
| 9-Fluorenyl Chloroformate (FMOC) | ICN #150200 |
| Sodium Borate | EM Science #SX 0355-1 |
| Boric Acid | Fisher #A-73 |
| Sodium Bicarbonate | ICN #194847 |
| Tetramethyl Ammonium Chloride | Fisher #04640-500 |
| Sodium Citrate | MCB #SX445 |
| Citric Acid anhydrous | Baker #0122-01 |
| Acetone | Burdick & Jackson #010-4 |
| Hydrochloric Acid, 0.1N | Fisher #SA48-500 |
| Calcium Chloride Dihydrate | Aldrich #22,350-6 |

Equipment

Transfer Pipettes, polyethylene (Samco #222)

Volumetric Flasks (25, 100, 250, 1000 ml)

Volumetric Pipet (10 ml)

Graduated Cylinders (100-1000ml)

HPLC reservoirs (500 ml, 1 or 2 liter)

Beakers

Magnetic stirrers/stir bars

Analytical (4-place) balance

Scintillation Vials

Centrifuge tubes, screw cap (100×16 mm) with caps

Autosampler vials (8×30 mm, 1 ml), with crimp caps

Safety: This method requires the use of a fume hood, and involves exposure to chemicals. Please review Safe Practices for Fume Hood Use and Chemical Spills.

| INSTRUMENT | MODEL | MANUFACTURER |
|---|---|---|
| Robot | Microlab® SPE | Hamilton |
| Pump/HPLC injector | HP 1100 | Agilent |
| Detector | RF10AXL | Shimadzu |
| Data System | Chemstation | Agilent |

Column

Phenomenex Luna 100×4.6 mm C-18(2) 3 micron # OOD-4251-EO

Preparation Of Reagents

Diluent (pH 8.3-8.5; 1000 ml).
1. Weigh 3.0 grams of Sodium Borate, 3.0 grams of Boric Acid, and 8.0 grams of Sodium Bicarbonate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step 1 to the water; stir until they are completely dissolved.
4. Quantitatively transfer the solution from step 3 to a 1-liter volumetric flask and dilute to volume with Milli-Q™ water; mix well. Stable for up to six (6) months.

Calcium Chloride Solution (100 grams).
1. Weigh 40 grams of Calcium Chloride Dihydrate into a tared 250 ml beaker.
2. Add 60 grams of Milli-Q™ water. Mix well. Store at ambient conditions in a capped glass bottle. Stable for up to 1 year.

Extraction Solvent (Pentane: Ethyl Acetate 80:20; 500 ml)

Safety: pentane and ethyl acetate are volatile and flammable. Perform the following operations in a Fume Hood.
1. Transfer 400 ml of pentane to a 500 ml HPLC reservoir bottle.
2. Add 100 ml ethyl acetate. Mix well. Store capped in/under the Fume Hood.

Mobile Phase (Buffer:Methanol:Acetonitrile 60:5:35, pH 3.2, 2 L)
1. Weigh 1.35 grams of Tetramethyl Ammonium Chloride, 3.65 grams of Citric Acid, and 1.60 grams of Sodium Citrate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step 1 to the water; stir until they are completely dissolved.
4. Quantitatively transfer the solution from step 3 to a 1 liter graduated cylinder and dilute to 1000 ml with Milli-Q™ water; mix well.
5. Transfer to a 2-liter HPLC mobile phase reservoir.
6. Add 200 ml Milli-Q™ water, 100 ml methanol and 700 ml acetonitrile. Add the latter two solvents slowly with vigorous stirring. Perform this operation in a hood, and wear personal protective equipment. Refer to the relevant Material Safety Data Sheets (MSDS) for specific details.
7. Degas the mobile phase by vacuum aspiration while stirring.

FMOC Reagent Solution (in Acetone)
1. Weigh 0.10 grams of FMOC reagent into a tared 100 ml volumetric flask.
2. Add acetone to dissolve and dilute to volume with same. Mix well. Perform this operation in a hood. Wear PPE specified in the MSDS for the chemicals.
3. Store refrigerated for no more than six (6) months.

Acid Solution for Sample Extraction (5% HCl)
1. Add 100 ml of Milli-Q™ water into a 200ml volumetric.
2. Add 4 ml of 1N HCl to volumetric.
Bring to volume with Milli-™ Water.

Preparation of Internal Standard (Aminoisobutyric Acid)

ISTD A—Internal Standard Stock A
1. Weigh 0.5 grams of aminoisobutyric acid into a tared 250 ml volumetric
2. Add 25 ml of 1.0N HCl and about 100 ml Milli-Q™ water. Mix by swirling until dissolved.
Dilute to volume with Milli-Q™ water and mix well. Store refrigerated for no more than six (6) months.

ISTD B—Working Internal Standard Solution B (This Solution is Added to Calibration Standards)
1. Pipet 1 ml of Internal Standard Stock A into a 100 ml volumetric flask.
2. Dilute to volume with Milli-Q water. Stable for one month.

Preparation of Calibration Standard(s)

Stock Calibration Solution

Into a tared 50 ml volumetric, weigh 0.100 g (+/−0.001 g) asparagine and 0.100 g (+/−0.001 g) aspartic acid. Add 25 mL Milli-Q™ water and 1 mL 1 N HCl. Place in sonic bath until dissolved, then bring to volume with Milli-Q™ H2O. Solution is good for 6 months refrigerated.

Working Standards

Prepare the Following Working Calibration Standards:

| Std # | mL stock | final volume (mL) | ppm |
|---|---|---|---|
| 1 | 5 | 200 | 50 |
| 2 | 5 | 100 | 100 |
| 3 | 1 | 10 | 200 |
| 4 | 3 | 10 | 600 |

Solutions are good for one month refrigerated.

Preparation of Samples
1. Weigh 1 g of sample into 125 ml Erlenmeyer flask.
2. Add 48.0ml of 5% HCl solution to each sample.
3. Add 2 ml ISTD A to each sample.
4. Cover each flask with aluminum foil and place in 60 C water bath for 30 minutes.
5. Add 10 mL dicloroethane to each sample.
6. Homogenize sample for 60 seconds.
7. Pour portion of sample into 30 ml centrifuge tube.
8. Centrifuge at 10000 rpm for 32 minutes at 5° C. The supernatant is used in "Samples—Diluting" step 1.

Preparation of Standards and Samples

Three Microlab® methods are run in order to dilute the samples/standards, add the internal standard, and form the FMOC derivative. These are summarized below.

| Operation | Microlab method used |
| --- | --- |
| Dilution | TRANSDIL |
| Addition of Internal Standard | ADDISTD |
| Formation of FMOC derivative | ADDFMOC |

Preparation Of Samples And Standards Using Microlab® Robot

Step 1: Standards—Adding ISTD and Dilution Step
1. Prepare two sets of tubes for each standard. Place approximately 2 mL of standard in one set of tubes, place these filled tubes on the left most position of the Microlab®.
2. Place the rack with empty tubes in the rightmost rack position of the Microlab®.
3. Fill a 20 ml glass (scintillation) vial with Working Internal Standard Solution B and place on the Microlab® workspace.
4. Select method ADDISTD. (Mixes 200 ul ISTD B, 50 ul standard solution, to 4000 ul total volume with Milli-Q™ water).
5. Execute the method.
6. Remove the tube set from the left position and set aside for discard.
7. Remove the Working Internal Standard Solution from the Microlab® work space and refrigerate.
   Set aside right side tubes for step 3.

Step 2: Samples—Dilution Step (ISTD was Already Added During Sample Preparation)
   1. Prepare two sets of tubes for each sample. Place approx. 2 mL of sample in one set of tubes, place these filled tubes on the left most position of the Microlab®.
   2. Place the rack with the empty tubes in the rightmost rack position of the Microlab®.
   3. Select method TRANSDIL. (Set # of samples, 50 ul for amount of sample, and 4000 ul for final dilution amount with Milli-Q™ water.)
   4. Execute the method.
   5. Remove the tube set from the left position and set aside for discard.
   Set aside right side tubes for step 3.

Step 3: Addition of FMOC Reagent—Making Fluorescent Derivative
1. Prepare a rack of 100×16 mm screw-cap tubes.
2. Place the rack in the rightmost rack position of the Microlab®.
3. Place standard and sample tubes from above dilution steps in leftmost rack position of Microlab®.
4. Transfer an aliquot (22 mL) of FMOC reagent solution to a glass scintillation vial. Add approximately 100 µL of 40% Calcium Chloride solution; mix well. (Calcium chloride is added to make the FMOC reagent "charged"—necessary for detection by Microlab®).
5. Place the vial on the Microlab® workspace.
6. Select method ADDFMOC.
7. Switch syringes 1 & 2 from water to Diluent (pH 8.3-8.5).
8. Perform a wash of at least five (5) cycles for syringes 1 & 2 using Diluent (pH 8.3-8.5)
9. Execute method ADDFMOC. (Mixes 450 ul of FMOC solution, 250 ul sample from ADDISTD above to final volume of 1300 ul with diluent solution).
10. Remove the tube set from the SAMPLE rack position and set aside.
11. Remove the FMOC reagent solution from the Microlab® workspace and refrigerate.
13. Remove the tube set from the rightmost position and place in fume hood. Let stand for at least 10 minutes or until solution is clarified (but no longer than 20 minutes).
14. Add 2 ml of Extraction Solvent to each tube. Cap and vortex at high speed for two (2) minutes to extract unreacted FMOC reagent.
15. Prepare another tube set of 55×16 mm tubes. Add 1 ml of mobile phase solution to each tube.
16. Transfer the 1.0 mL of aqueous (lower) layer from the centrifuge tubes to the 55×16 mm tubes.
17. Discard the upper (organic) layer.
18. Transfer samples to autosampler vials and seal.

Chromatography

Operating Conditions
   HP 100 with Chem Station software

| | |
| --- | --- |
| Detector: | Waters 474 Scanning Fluorescence detector |
| | Mode: Norm |
| | Signal: 0.0000 |
| | Wavelength: Ex 260 |
| | Em 313 |
| | Gain: 10 |
| | Atten: 1 |
| | Response: FST |
| Column: | Phenomex Luna C18 (2) 100 × 4.6 mm 3u |

LC Method

Flow: 1.000 ml/min

Isocratic run (see preparation of reagents—Mobile Phase)

Injection volume: 10.0 ul

Temperature settings: not controlled

Calculations
   Sample solutions are calculated against a standard curve of known amounts using area counts:

$$y=mx+b$$

$$y(\text{ratio asparagine}/ISTD)=m(\text{slope})\times(\text{asparagine concentration})+b(y\text{-intercept})$$

$$(y-b)/m=x$$

ppm asparagine=(area aspargine/area ISTD−intercept)/slope

Example:
   ppm asparagine=(215.45436/551.828−−0.0165)/0.0023=176.93 ppm
   [ppm=ug/mL]

Correction for Dilution/Homogenization in Sample Preparation Step $$ug/g \text{ aspargine} = ppm \text{ aspargine found} \times \frac{\text{mL sample dilution(50)}}{\text{grams of sample}}$$

[ppm=ug/mL]

Example:

$$ug/g \text{ aspargine} = 176.93 \ ppm \times \frac{50 \text{ mls}}{1.0083 \text{ g}} = 8773.65 \ ug/g$$

Run Acceptability Criteria:
the Check Sample of Working Reference Material accuracy must be within 10% of known result for asparagine.
the linearity of the calibration curve ($r^2$) must be 0.995 or greater.

Sample Chromatogram of LC Analysis

Figure 3:
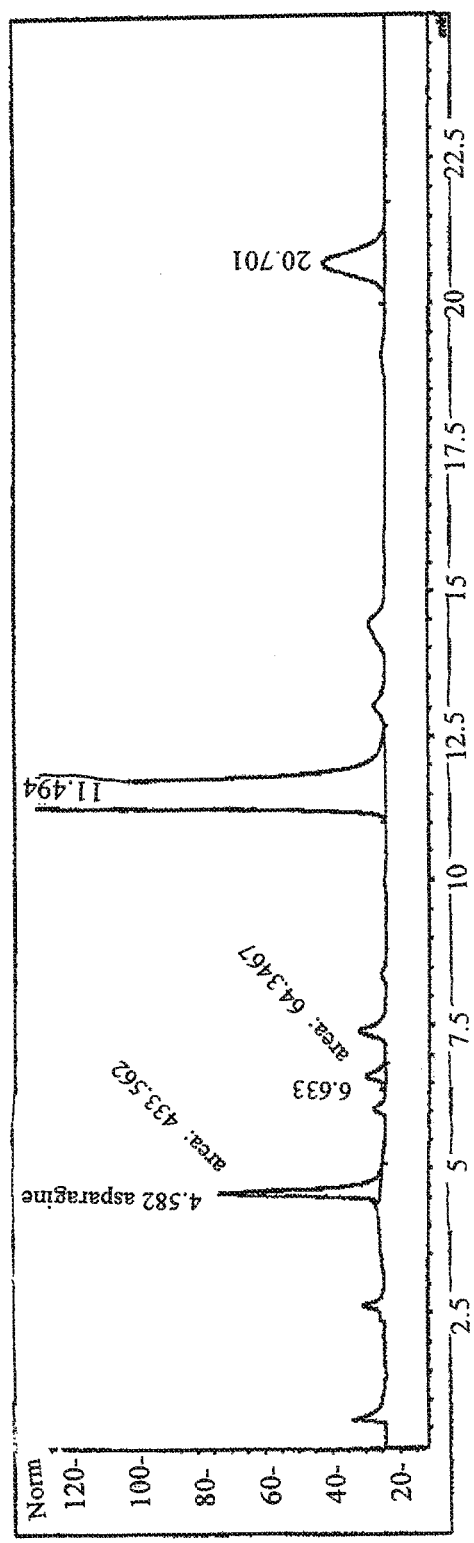
FIG. 3 sets forth a sample chromatogram for LC analysis of asparagine and aspartic acid. The x-axis represents retention time and the y-axis represents response.

FIG. 3 sets forth a sample chromatogram of LC analysis.

| RT | Compound |
|---|---|
| 4.5 min | asparagine |
| 6.6 min | aspartic acid |
| 11.5 min | FMOC reagent |
| 20.7 min | ISTD |

3. % Reduction of Acrylamide
% Reduction Acrylamide=[(Acrylamide level in control sample−Acrylamide level in enzyme-treated sample)/Acrylamide level in control sample]×100.

The control sample is prepared in exactly the same manner as the enzyme-treated sample, with the exception that enzyme is not added.

4. % Reduction of Asparagine
% Reduction Asparagine=[(Asparagine level in control sample−Asparagine level in enzyme-treated sample)/Asparagine level in control sample]×100.

The control sample is prepared in exactly the same manner as the enzyme-treated sample, with the exception that enzyme is not added.

EXAMPLES

The following examples are illustrative of the present invention but are not meant to be limiting thereof.

Example 1

Dehydrated Potato Product

Russet baking potatoes are rinsed with water then placed in a pot of boiling water. The potatoes are boiled (submerged) for 1 hour. The boiled potatoes are removed from the water, peeled, then the flesh is mashed. To 15 g of the mashed potatoes is added 45 g of water and the mixture is homogenized until uniform and such that no lumps are present. 50 units of asparaginase (purchased from Sigma-Aldrich catalog #A2925) are added to this homogenized solution and the sample is shaken every five minutes for a total of 30 minutes incubation.

The amount of asparaginase added is based upon the following: Enzymes are sold in units of activity. One unit of activity is defined as follows: One unit will liberate 1.0 µmole of ammonia from L-asparagine per minute at pH 8.6 at 37° C. Potatoes generally contain from about 0.2% to about 0.4% free asparagine. Thus, 15 g of potatoes contain from about 0.03 g to about 0.06 grams of asparagine, which equals from about 227 to about 454 µmoles of asparagine. Thus, under optimum conditions, 50 units of asparaginase will consume about 500 µmoles of asparagine in about 10 minutes. However, because the matrix of mashed potatoes may not provide optimum conditions for the enzyme, 30 minutes is allowed for the incubation time to allow as much asparagine as possible to degrade and to result in a lower acrylamide level in the final cooked product.

After the 30-minute incubation, the product is microwaved (Panasonic microwave, model NN-S5488A) on high for 2-minute increments for a total of 10 minutes until dry (and brown). Compared to dehydrated potato products prepared by the exact same process but without the enzyme (control sample), the enzyme-treated dehydrated potato product results in greater than a 99% reduction in acrylamide when analyzed for acrylamide using the method set forth herein.

| Dehydrated Potato Products | Acrylamide (ppb) |
|---|---|
| Control | 20,500 |
| Enzyme-treated | 164 |
| Percent Reduction | >99 |

Example 2

Potato Chips

Potato chips having reduced levels of acrylamide can be made using raw potato slices. Peel Atlantic potatoes and slice to ~1.1 mm thickness. Rinse and pad dry. Blanch potato slices in 165° F. water for fifteen seconds. Cool and drain blanched slices. Soak 100 grams of blanched potato slices in 250 ml of distilled/deionized water containing asparaginase, having 100 units of activity, for one hour. Agitate sample by swirling for 1 minute every 8 minutes. Heat using a microwave oven (Panasonic microwave, model NN-S5488A) on a setting of high for 2 minutes followed by three 10 second washings with about 800 ml of cool tap water. Fry the treated potato slices in a fryer set at 375° F. for 60 seconds. (Example 2A) Two more batches of potato chips are made as above, with the exception that the blanch time is changed to 60 seconds (Example 2B) and 180 seconds (Example 2C).

Control samples are prepared in the same manner used to prepare Examples 2A, B, and C above, with the exception that the asparaginase is not added to the soaking solution.

The samples and the controls are analyzed for acrylamide using the method set forth herein.

| | 2A | 2B | 2C |
|---|---|---|---|
| Blanch time (seconds) | 15 | 60 | 180 |
| Acrylamide (ppb) in control samples | 281 | 156 | 50 |

|  | 2A | 2B | 2C |
|---|---|---|---|
| Acrylamide (ppb) in samples treated with asparaginase | <5 | 5 | <5 |
| Percent reduction | >98 | 97 | >90 |

Conventional potato chips do not undergo a blanching step. Thus, potato chips having a blanching step are not known in the art. The example above demonstrates that superior results can be obtained by employing the novel combination of blanching and enzyme addition to the potato-chip making process. Commercially produced potato chips have acrylamide levels much higher than the control samples used above. The control samples above employed the novel blanching step (and soaking with water instead of enzyme) to more fully demonstrate the added effect that enzyme treatment has on the process.

A potato chip made exactly as above except without the novel steps of blanching and enzyme treatment results in potato chips having an acrylamide level of 1079 ppb. Thus it can be seen that enzyme treatment, especially when blanching is employed, is especially effective in reducing the level of acrylamide.

Example 3

French Fries

French fries having reduced levels of acrylamide can be made using raw potato strips. Peel Atlantic potatoes and cut into strips having a cross-sectional area of about 8 mm×8 mm. Rinse and pad dry. Blanch potato strips in 165° F. water for one minute. Cool and drain blanched strips. Soak 100 grams of blanched potato strips in 250 ml of distilled/deionized water containing asparaginase, having 100 units of activity, for one hour. Agitate sample by swirling for 1 minute every 8 minutes. Heat using a microwave oven (Panasonic microwave, model NN-S5488A) on a setting of high for 2 minutes followed by three 10 second washings with about 800 ml of cool tap water. Fry the treated potato strips in a fryer set at 375° F. for 60 seconds. (Example 3A) Two more batches of French fries are made as above, with the exception that the blanch time is changed to 3.5 minutes (Example 3B) and 7 minutes (Example 3C).

Control samples are prepared in the same manner used to prepare Examples 3A, B, and C above, with the exception that the asparaginase is not added.

The samples and the controls are analyzed for acrylamide using the method set forth herein.

|  | 3A | 3B | 3C |
|---|---|---|---|
| Blanch time (minutes) | 1 | 3.5 | 7 |
| Acrylamide (ppb) in control samples | 130 | 84 | 57 |
| Acrylamide (ppb) in samples treated with asparaginase | 30 | 17 | 12 |
| Percent reduction | 77 | 80 | 79 |

Example 4

Article of Commerce

The potato chips of Example 2A are packaged in a bag for sale to consumers. Printed on the bag is a message stating, "Acrylamide-free product!"

Example 5

Article of Commerce

The potato chips of Example 2B are packaged in a bag for sale to consumers. Printed on the bag is a message stating, "Low in acrylamide!"

Example 6

Article of Commerce

The potato chips of Example 2C are packaged in a bag for sale to consumers. Printed on the bag is a message stating, "Acrylamide reduced by over 90%!" A television commercial for the chips communicates the message, "Our chips are lower in acrylamide!"

Example 7

Article of Commerce

Uniformly-shaped fabricated potato crisps having less than 100 ppb acrylamide are packaged in a cylindrical canister for sale to consumers. A television commercial for the crisps communicates the message, "Acrylamide-reduced!"

Example 8

Article of Commerce

The French fries of Example 3B are packaged in a paper sleeve having an open end, from which the fries protrude, for sale to consumers. A sign posted inside the retail establish where the French fries are sold reads, "Our fries contain reduced levels of acrylamide!"

Example 9

Article of Commerce

The French fries of Example 3C are packaged in a paper sleeve having an open end, from which the fries protrude, for sale to consumers. A sign posted inside the retail establish where the French fries are sold reads, "Our fries contain reduced levels of acrylamide!"

Example 10

Article of Commerce

The potato chips of Example 2C are packaged in a bag for sale to consumers. Printed on the bag is a message stating, "Made from ingredients low in asparagine!"

Example 11

Dehydrated Potato Product

Russet baking potatoes are rinsed with water then placed in a pot of boiling water. The potatoes are boiled (submerged)

for 1 hour. The boiled potatoes are removed from the water, peeled, then the flesh is mashed. To 15 g of the mashed potatoes is added 45 g of water and the mixture is homogenized until uniform and such that no lumps are present.

200 units of glutaminase are added to this homogenized solution and the sample is shaken every five minutes for a total of 30 minutes incubation.

After the 30-minute incubation, the product is microwaved (Panasonic microwave, model NN-S5488A) on high for 2-minute increments for a total of 10 minutes until dry (and brown). Compared to dehydrated potatoes prepared by the exact same process but without the enzyme (control sample), the enzyme-treated dehydrated potato product results in greater than a 10% reduction in acrylamide when analyzed for acrylamide using the method set forth herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making potato products having reduced levels of acrylamide, comprising:
   cooking potatoes;
   adding an asparagine-reducing enzyme to the cooked potatoes;
   forming a wet mash;
   drying the mash to form dehydrated potato products.

2. The method of claim 1 further comprising forming a dough from the dehydrated potato products and adding additional asparagine-reducing enzyme to the dough.

3. The method of claim 1 wherein the dehydrated potato products are selected from the group consisting of potato flakes, flanules, granules, agglomerates, sheets, pieces, bits, flour, and particulates.

4. The method of claim 1 wherein the potatoes have less than 2% reducing sugars.

5. The method of claim 1 wherein the cooking is by submersion in water or steam.

6. The method of claim 1 wherein the potatoes are potato slices that are cooked with steam having a temperature of from about 200° F. to about 250° F. from about 12 to about 45 minutes.

7. The method of claim 1 wherein the potatoes are shoestring cut potato pieces that are cooked with steam having a temperature of from about 200° F. to about 250° F. for about 7 to about 18 minutes.

8. The method of claim 1 further comprising adding optional ingredients to the wet mash.

9. The method of claim 8 wherein the optional ingredients comprise starch.

10. The method of claim 1 wherein the dehydrated potato products are flakes and wherein the drying comprises freeze drying, drum drying, resonant drying, pulse flow drying, infrared drying, or a combination thereof.

11. The method of claim 1 wherein the dehydrated potato products are granules and wherein the drying comprises air lift drying, fluidized bed drying, or a combination thereof.

12. The method of claim 1 further comprising producing fabricated chips from the dehydrated potato products.

13. The method of claim 1 further comprising rehydrating the dehydrated potato products.

14. The method of claim 13 further comprising producing mashed potatoes, potato patties, potato pancakes, extruded French Fries, or potato sticks from the rehydrated potato products.

15. The method of claim 1 wherein the asparagine-reducing enzyme is asparaginase.

16. The method of claim 1 wherein the level of acrylamide is reduced by at least about 10% than if the asparagine-reducing enzyme had not been added.

17. The method of claim 1 wherein the level of acrylamide is reduced by at least about 50% than if the asparagine-reducing enzyme had not been added.

18. The method of claim 1 wherein the level of acrylamide is reduced by at least about 90% than if the asparagine-reducing enzyme had not been added.

19. The method of claim 1 wherein said asparagine-reducing enzyme is an enzyme capable of hydrolyzing the amide group of free asparagine.

20. A method for reducing the level of acrylamide in potato chips, comprising:
   optionally peeling potatoes;
   optionally washing potatoes;
   slicing potatoes to form potato slices;
   optionally rinsing the potato slices;
   optionally blanching the potato slices;
   optionally cooling the potato slices;
   adding an acrylamide-reducing enzyme to the potato slices;
   optionally drying the potato slices; and
   frying the potato slices to form potato chips.

* * * * *